(12) United States Patent
Lee

(10) Patent No.: US 9,119,591 B2
(45) Date of Patent: *Sep. 1, 2015

(54) 3D ULTRASOUND SYSTEM AND METHOD FOR OPERATING 3D ULTRASOUND SYSTEM

(71) Applicant: SAMSUNG MEDISON CO., LTD., Gangwon-do (KR)

(72) Inventor: Kwang Hee Lee, Daejeon (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/927,974

(22) Filed: Jun. 26, 2013

(65) Prior Publication Data

US 2013/0281860 A1 Oct. 24, 2013

Related U.S. Application Data

(63) Continuation of application No. 13/044,195, filed on Mar. 9, 2011, now Pat. No. 8,491,480.

(30) Foreign Application Priority Data

May 31, 2010 (KR) ........................ 10-2010-0051124

(51) Int. Cl.
*A61B 8/00* (2006.01)
*A61B 8/08* (2006.01)
(Continued)

(52) U.S. Cl.
CPC ............. *A61B 8/5223* (2013.01); *A61B 8/0866* (2013.01); *A61B 8/483* (2013.01); *A61B 8/54* (2013.01); *G01S 15/8993* (2013.01); *G01S 7/52063* (2013.01)

(58) Field of Classification Search
CPC ............. A61B 8/5223; A61B 8/52063; A61B 8/8993; A61B 8/483; A61B 8/54
USPC ........................... 600/437–469; 382/128–132
See application file for complete search history.

(56) References Cited

U.S. PATENT DOCUMENTS 6,346,124 B1 2/2002 Geiser et al.
6,716,175 B2 4/2004 Geiser et al.
(Continued)

FOREIGN PATENT DOCUMENTS

JP 2010-259527 A 11/2010
KR 10-2008-0004775 A 1/2008
WO 2009/136332 A2 11/2009

OTHER PUBLICATIONS

Korean Office Action, and English translation thereof, issued in Korean Patent Application No. 10-2011-0052396 dated Jul. 25, 2012.
(Continued)

*Primary Examiner* — Sanjay Cattungal
(74) *Attorney, Agent, or Firm* — McDermott Will & Emery LLP

(57) ABSTRACT

A 3-dimensional (3D) ultrasound system and a method for operating a 3D ultrasound system are provided. A 3D ultrasound system includes an extractor, a processor, and a controller. The extractor scans an image of an object in a human body, and extracts a region of interest (ROI) image in an inputted ROI with respect to a selected image. The processor detects edges from a plurality of side images of the object with respect to the ROI image. The controller measures the thickness of the image using the detected edges.

18 Claims, 3 Drawing Sheets

(51) Int. Cl.
*G01S 15/89* (2006.01)
*G01S 7/52* (2006.01)

(56) References Cited

U.S. PATENT DOCUMENTS

| | | |
|---|---|---|
| 6,939,301 B2 | 9/2005 | Abdelhak |
| 7,022,073 B2 | 4/2006 | Fan et al. |
| 7,041,059 B2 | 5/2006 | Chalana et al. |
| 7,087,022 B2 | 8/2006 | Chalana et al. |
| 7,520,857 B2 | 4/2009 | Chalana et al. |
| 7,616,818 B2 | 11/2009 | Dewaele |
| 7,744,534 B2 | 6/2010 | Chalana et al. |
| 2002/0133075 A1 | 9/2002 | Abdelhak |
| 2004/0024302 A1 | 2/2004 | Chalana et al. |
| 2004/0127796 A1 | 7/2004 | Chalana et al. |
| 2005/0251039 A1 | 11/2005 | Chalana et al. |
| 2006/0235301 A1 | 10/2006 | Chalana et al. |
| 2008/0146932 A1 | 6/2008 | Chalana et al. |
| 2008/0242985 A1 | 10/2008 | Chalana et al. |

OTHER PUBLICATIONS

Korean Office Action with English translation issued in Korean Application No. 10-2011-0052396 Feb. 25, 2013.
Korean Office Action, w/ English translation thereof, issued in Korean Patent Application No. KR 10-2011-0052396 dated May 8, 2013.
Korean Office Action issued in Application No. 10-2013-0064968 dated May 30, 2014.
G. Clementschitsch et al., "Comparison between two-and three-dimensional ulstrasound measurements of nuchal translucency," Ultrasound Obstet. Gynecol. 2001; vol. 18, pp. 475-480.
European Search Report issued in European Application No. 11154696.6-1812 dated Jan. 31, 2014.
Karl Krissian et al., "Speckle-Constrained Filtering of Ultrasound Images", This work was supported by CIMIT grant and NIH P41-RR13218 (NAC).
Japanese Office Action issued in Japanese Application No. 2011-093531 dated Oct. 28, 2014, w/English translation.
Korean Office Action issued in Korean Application No. 10-2013-0064968 dated Jan. 26, 2015, with English Translation and Certificate of Translation.

3D ULTRASOUND SYSTEM AND METHOD FOR OPERATING 3D ULTRASOUND SYSTEM

CROSS-REFERENCE TO RELATED APPLICATIONS

This application is a Continuation of U.S. application Ser. No. 13/044,195, filed on Mar. 9, 2011, which claims the benefit of Korean Patent Application No. 10-2010-0051124, filed on May 31, 2010, in the Korean Intellectual Property Office, disclosures of which are incorporated herein by reference.

BACKGROUND

1. Field of the Invention

The present invention relates to a 3-dimensional (3D) ultrasound system and a method for operating a 3D ultrasound system capable of detecting edges from a plurality of side images of an object in a human body with respect to a region of interest (ROI) image in an image of the object and automatically measuring the thickness of the image using the detected edges.

2. Description of the Related Art

An ultrasound system is an apparatus that irradiates an ultrasound signal from a surface of a human body towards a target part, that is, an object such as a fetus, an internal organ, and the like, under the body surface and obtains an image of a monolayer or blood flow in soft tissue from information in the reflected ultrasound signal. The ultrasound system has been widely used together with other image diagnostic systems such as X-ray diagnostic systems, computerized tomography (CT) scanners, magnetic resonance image (MRI) systems and nuclear medicine diagnostic systems because of its various merits such as a small size, a low price, real-time image display, and high stability through elimination of any radiation exposure.

Also, a method for diagnosing a Down's syndrome fetus is to measure the thickness of a fetus' nuchal translucency (NT) through an ultrasound system. Here, the ultrasound system may measure the thickness of the fetus' NT, using a figure template controlled according to a combination of a trackball and a set button, controlled by a user.

Accordingly, when the thickness of an object or a partial region is measured using the ultrasound system, intervention of a user is unavoidable, and it is impossible to precisely measure the thickness of the object due to the intervention of the user.

Therefore, an ultrasound system capable of easily providing a precise measurement result by automating a series of processes for measuring the thickness of an object, and capable of minimizing the intervention of a user, is desired.

SUMMARY

An aspect of the present invention provides a 3-dimensional (3D) ultrasound system and a method for operating a 3D ultrasound system, in which edges are detected from a plurality of side images of an object in a human body with respect to a region of interest (ROI) image in an image of the object, and the thickness of the image is automatically measured using the detected edges, to enable a precise measurement result of the thickness of the image to be provided.

According to an aspect of the present invention, there is provided a 3D ultrasound system including an extractor to scan an image of an object in a human body and to extract an ROI image in an inputted ROI with respect to a selected image, a processor to detect edges from a plurality of side images of the object with respect to the ROI image, and a controller to measure the thickness of the image using the detected edges.

According to an aspect of the present invention, there is provided a method for operating a 3D ultrasound system, the method including scanning an image of an object in a human body and extracting an ROI image in an inputted ROI with respect to a selected image, detecting edges from a plurality of side images of the object with respect to the ROI image, and measuring the thickness of the image using the detected edges.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
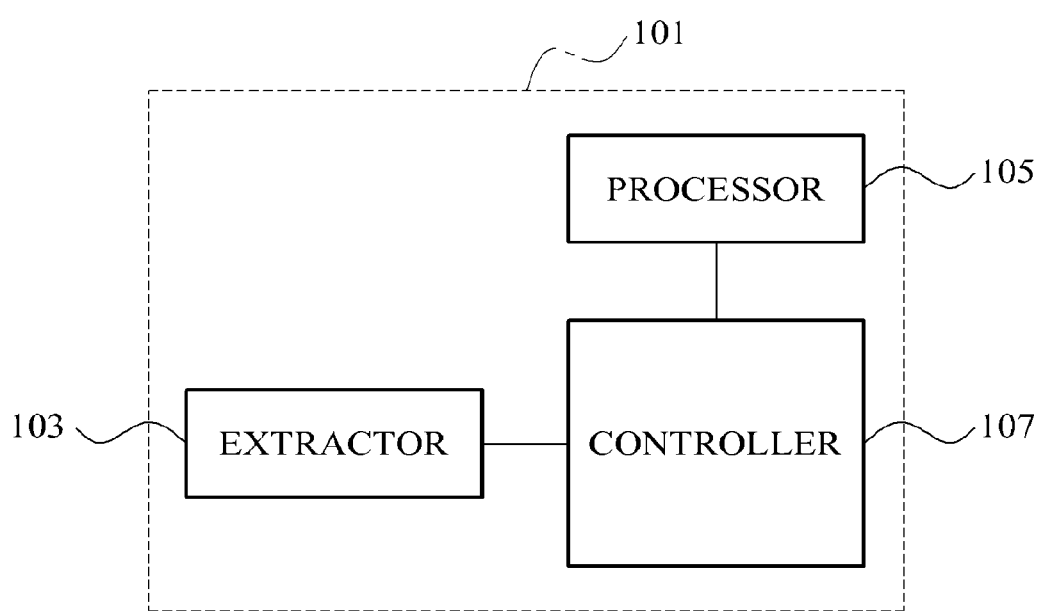
FIG. 1 is a block diagram illustrating a configuration of a 3-dimensional (3D) ultrasound system according to an embodiment of the present invention.

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

FIG. 1 is a block diagram illustrating a configuration of a 3-dimensional (3D) ultrasound system 101 according to an embodiment of the present invention.

Referring to FIG. 1, the 3D ultrasound system 101 includes an extractor 103, a processor 105, and a controller 107.

The extractor 103 may scan an image of an object in a human body and extract a region of interest (ROI) image in an inputted ROI with respect to a specific image. Here, the object in the human body may be a fetus, blood vessel, an internal organ, and the like. The ROI defines a partial region in which the thickness of a specific image in an object is to be measured, and may be inputted by a user.

For example, in a case where the object is a fetus, the extractor 103 may extract an ROI image in the ROI inputted to include the fetus' nuchal translucency (NT).

The extractor 103 may perform denoising with respect to the extracted ROI image, so as to clarify an image in a region, of which thickness is to be measured.

As an example, the processor 105 detects edges from a plurality of side images of the object with respect to the ROI image. In this instance, the processor 105 may detect first edges of which brightness intensity is changed from a large value to a small value from the plurality of side images, and may detect second edges of which brightness intensity is change from a small value to a large value from the plurality of side images. That is, the processor may detect first edges at which a bright image is changed into a dark image from the plurality of side images, and may detect second edges at which a dark image is changed into a bright image from the plurality of side images. The change in brightness is a result of the intensity of a specific image to be measured, for example, the intensity of the fetus' NT, is relatively darker than that in a peripheral region. Accordingly, the processor 105 may detect edges at a boundary of the fetus' NT.

The processor 105 may detect a first true edge by connecting the first edges detected from the plurality of side images, and may detect a second true edge by connecting the second edges detected from the plurality of side images. The first edge and the second edge may be curved lines, and the first true edge and the second true edge may be curved surfaces formed in a vertical direction relative to the side images.

Here, the processor 105 may detect the first true edge and the second true edge based on the first edge and the second edge of a side image positioned in the middle of the plurality of side images, in consideration of a connection with a first edge and a second edge of other side images.

As another example, in a case where the object is a fetus, the processor 105 may detect a region of which brightness intensity has a small value based on a selected brightness intensity, that is, a region of which a bright intensity is darker than the selected brightness intensity, from the plurality of side images with respect to the ROI image, and determine a region of the fetus' NT from the detected region. Then, the processor 105 may detect a first edge corresponding to an upper boundary in the region of the fetus' NT and a second edge corresponding to a lower boundary in the region of the fetus' NT. In this instance, the processor 105 may detect the first edge and the second edge in the region of the fetus' NT, detected from the side image corresponding to a sagittal view.

Here, the processor 105 may perform 3D labeling with the region of which a bright intensity has a small value based on the selected brightness intensity from the plurality of side images, and determine a label having the largest volume among labels as the region of the fetus' NT. The processor 105 may precisely detect boundaries, for example, upper and lower boundaries, in the region of the fetus' NT by using a 3D active contour or levelset algorithm.

The controller 107 may measure the thickness of an image using the detected edges. The controller 107 may detect the thickness of the image by measuring a distance between the first edge and the second edge with respect to a plurality of side images.

The controller 107 may calculate at least one of the mean, standard deviation, minimum distance and maximum distance of the distances between a plurality of first edges and a plurality of second edges and then display at least one of the mean, standard deviation, minimum distance and maximum distance on a screen. In a case where the maximum distance is calculated among the distances between the plurality of first edges and the plurality of second edges, the controller 107 may distinctly display a boundary between the first edge and the second edge of the side image corresponding to the maximum distance. For example, the controller 107 may designate '+' at the boundary between the first edge and the second edge of the side image corresponding to the maximum distance and thus, easy detection of the position and thickness of an image having a thickness corresponding to the maximum distance is possible.

In addition, before measuring the thickness of an image, the controller 107 may rotate the image of the scanned object, using gradients of the plurality of side images of the object with respect to the ROI image, thereby more precisely measuring the thickness of the image. In further detail, the controller 107 may control the slope of the image by calculating the mean of gradients of the side image positioned in the middle of the plurality of side images of the object with respect to the ROI image and rotating the image of the scanned object by a difference between the mean of the gradients and the horizontal direction, that is, zero degrees.

According to the present embodiment, edges are detected from a plurality of side images of an object in a human body with respect to an ROI for an image of the object, and the thickness of the image is automatically measured using the detected edges, to enable a precise measurement result of the thickness of the image to be provided.

Figure 2:
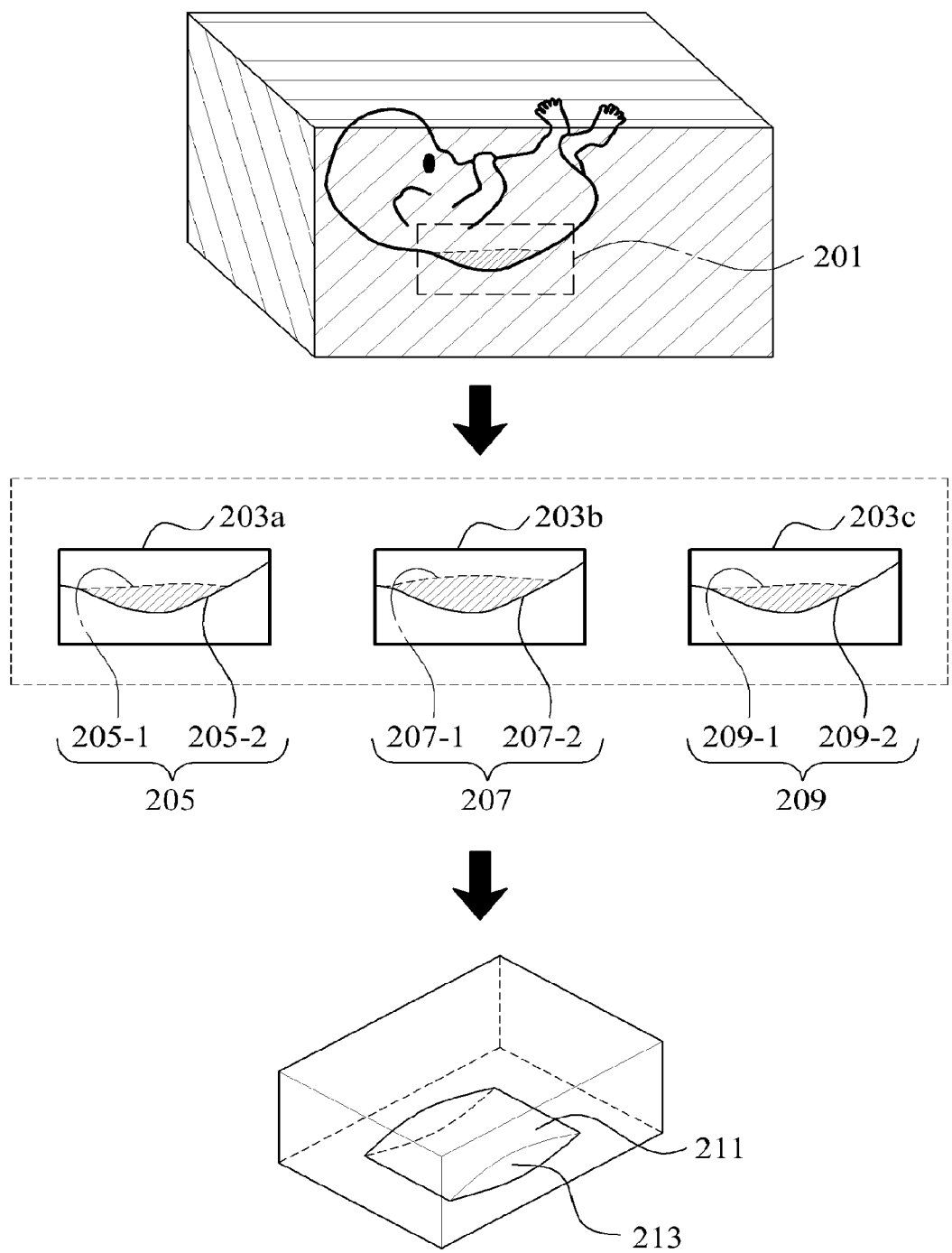
FIG. 2 is a diagram illustrating an example of measuring the thickness of a specific image in a 3D ultrasound system according to the embodiment of the present invention.

FIG. 2 is a diagram illustrating an example of measuring the thickness of a specific image in a 3D ultrasound system according to the embodiment of the present invention.

Referring to FIG. 2, the 3D ultrasound system may scan an image of the object in a human body and extract an ROI image in an ROI 201 including a fetus' NT.

The 3D ultrasound system may detect edges 205, 207 and 209 from a plurality of side images 203a, 203b and 203c of the object with respect to the ROI 201. In this instance, the 3D ultrasound system may detect first edges 205-1, 207-1 and 209-1 at which a bright image is changed into a dark image, and may detect second edges 205-2, 207-2 and 209-2 at which a dark image is changed into a bright image.

The 3D ultrasound system may detect a first true edge 211 that is a curved surface by connecting the first edges with respect to the plurality of side images, and may detect a second true edge 213 that is a curved surface by connecting the second edges with respect to the plurality of side images.

The 3D ultrasound system may measure distances between the first edges 205-1, 207-1 and 209-1 and the second edges 205-2, 207-2 and 209-2 with respect to the plurality of side images 203a, 203b and 203c, and detect the maximum distance among the measured distances as the thickness of the fetus' NT.

Figure 3:
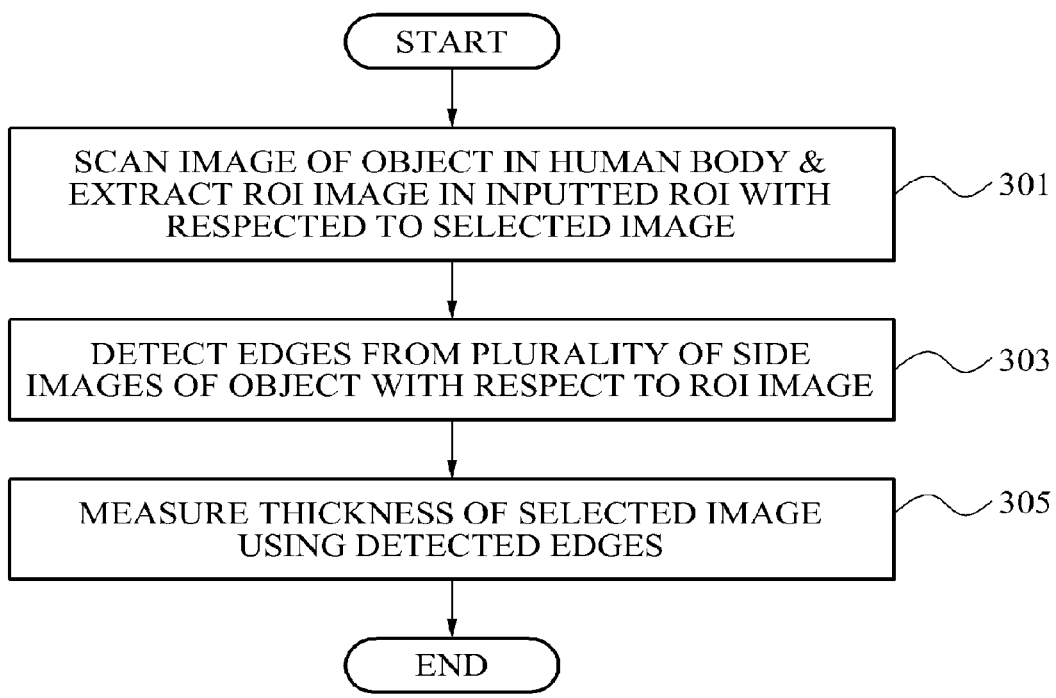
FIG. 3 is a flowchart illustrating a method for operating a 3D ultrasound system according to an embodiment of the present invention.

FIG. 3 is a flowchart illustrating a method for operating a 3D ultrasound system according to an embodiment of the present invention.

Referring to FIG. 3, in operation 301, the 3D ultrasound system scans an image of an object in a human body and extracts an ROI image in an inputted ROI with respect to a specific image. Here, the ROI defines a partial region in which the thickness of a specific image in an object is to be measured, and may be inputted by a user.

For example, in a case where the object is a fetus, the 3D ultrasound system may extract an ROI image in the ROI inputted to include the fetus' NT.

In operation 303, the 3D ultrasound system detects edges from a plurality of side images of the object with respect to the ROI image.

Specifically, the 3D ultrasound system may detect first edges of which bright intensity is changed from a large value to a small value from the plurality of side images, and may detect second edges of which bright intensity is changed from a small value to a large value from the plurality of side images.

Subsequently, as an example, the 3D ultrasound system may detect a first true edge that is a curved surface by connecting the first edges with respect to the plurality of side images, and may detect a second true edge that is a curved surface by connecting the second edges with respect to the plurality of side images.

The 3D ultrasound system may rotate the image of the scanned object, using gradients of the plurality of side images of the object with respect to the ROI image, thereby more precisely measuring the thickness of the image. That is, the 3D ultrasound system may control the slope of the image by calculating the mean of gradients of a side image positioned in the middle of the plurality of side images of the object with respect to the ROI image, and by rotating the image of the scanned object by a difference between the mean of the gradients and the horizontal direction, that is, zero degrees.

As another example, in a case where the object is a fetus, the 3D ultrasound system may detect a region of which brightness intensity has a small value based on a selected brightness intensity, that is, a region of which bright intensity is darker than the selected brightness intensity, from the plurality of side images with respect to the ROI image, and determine a region of the fetus' NT from the detected region. Then, the 3D ultrasound system may detect a first edge corresponding to an upper boundary in the region of the fetus' NT, and a second edge corresponding to a lower boundary in the region of the fetus' NT. In this instance, the 3D ultrasound system may detect the first and second edges in the region of the fetus' NT, detected from the side image corresponding to a sagittal view.

In operation 305, the 3D ultrasound system measures the thickness of the selected image by using the detected edges. That is, the 3D ultrasound system may detect the thickness of the image by measuring distances between first and second edges with respect to the plurality of side images.

The 3D ultrasound system may calculate at least one of the mean, standard deviation, minimum distance, and maximum distance of the distances between a plurality of first edges and a plurality of second edges and then display at least one of the mean, the standard deviation, the minimum distance, and the maximum distance on a screen. In a case where the maximum distance is calculated among the distances between the plurality of first edges and the plurality of second edges, the 3D ultrasound system may distinctly display a boundary between the first edge and the second edge of the side image corresponding to the maximum distance.

As described above, according to embodiments, edges are detected from a plurality of side images of an object in a human body with respect to a region of interest (ROI) image in an image of the object, and the thickness of the image is automatically measured using the detected edges, to enable a precise measurement result of the thickness of the image to be provided.

The above-described exemplary embodiments of the present invention may be to recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A 3-dimensional (3D) ultrasound system, comprising:
an extractor configured to scan an image of an object and to extract a region of interest (ROI) image from the image of the object, the ROI image including a measurement region of the object;
a processor configured to detect a first edge and a second edge of a first side image and a first edge and a second edge of a second side image, the first and second side images being generated from the ROI image, detect a first true edge based on the first edge of the first side image and the first edge of the second side image, detect a second true edge based on the second edge of the first side image and the second edge of the second side image, and display the detected first and second true edges on a screen; and
a controller configured to measure the thickness of the measurement region based on a distance between the first edge and the second edge of one of the first side image and the second side image.

2. The 3D ultrasound system of claim 1, wherein, when the object is a fetus, the measurement region is the fetus' nuchal translucency (NT), and the extractor extracts the ROI image including the fetus' NT.

3. The 3D ultrasound system of claim 1, wherein the processor is configured to detect the first true edge by connecting the first edge of the first side image and the first edge of the second side image, and detects the second true edge by connecting the second edge of the first side image and the second edge of the second side image.

4. The 3D ultrasound system of claim 1, wherein, when the object is a fetus, the first side image corresponds to a sagittal view of the fetus, and the first and second edges of the first side image correspond to the fetus' nuchal translucency (NT).

5. The 3D ultrasound system of claim 1, wherein, when the object is a fetus, the measurement region is the fetus' nuchal translucency (NT), and the processor is configured to detect the measurement region from a region of which brightness intensity is smaller than a reference brightness intensity in the first side image, and detect the first edge corresponding to an upper boundary in the measurement region and the second edge corresponding to a lower boundary in the measurement region.

6. The 3D ultrasound system of claim 1, wherein the number of the second side image is at least one, and the processor detects a first edge and a second edge of the at least one second side image, the at least one second side image being generated from the ROI image, the controller is configured to obtain a plurality of measured distances by measuring a distance between the first edge and the second edge in each of a plurality of side images including the first side image and the at least one second image, and measure the thickness of the measurement region based on at least one of the mean, standard deviation, minimum distance, and maximum distance of the plurality of the measured distances.

7. The 3D ultrasound system of claim 1, wherein the controller obtains the maximum distance between the first edge and the second edge, and measures the thickness of the measurement region based on the maximum distance.

8. The 3D ultrasound system of claim 6, wherein the controller controls to distinctly display the first edge and the second edge of a max side image among the plurality of side images and the first edges and the second edges of the other side images, the measured distance of the maximum side image is the maximum distance.

9. A method for operating a 3D ultrasound system, the method comprising:
- scanning an image of an object and extracting a region of interest (ROI) image from the image of the object, the ROI image including a measurement region of the object;
- detecting a first edge and a second edge of a first side image, wherein the first side image is generated from the ROI image;
- detecting a first edge and a second edge of a second side image, the second side image being generated from the ROI image;
- detecting a first true edge based on the first edge of the first side image and the first edge of the second side image;
- detecting a second true edge based on the second edge of the first side image and the second edge of the second side image;
- measuring the thickness of the measurement region based on a distance between the first edge and the second edge of one of the first side image and the second side image; and
- displaying the detected first and second true edges on a screen.

10. The method of claim 9, wherein, when the object is a fetus, the measurement region is the fetus' nuchal translucency (NT), and the ROI image includes the fetus' NT.

11. The method of claim 9, wherein the detecting the first true edge comprises:
- detecting the first true edge by connecting the first edge of the first side image and the first edge of the second side image, and
- the detecting of the second true edge comprises detecting the second true edge by connecting the second edge of the first side image and the second edge of the second side image.

12. The method of claim 9, wherein, when the object is a fetus, the first side image corresponds to a sagittal view of the fetus, and the edge corresponds to the fetus' nuchal translucency (NT).

13. The method of claim 9, wherein:
- when the object is a fetus, the measurement region is the fetus' nuchal translucency (NT), and
- the detecting of the first and second edges of the first side image comprises:
  - detecting the measurement region from a region of which brightness intensity is smaller than a reference brightness intensity in the first side image; and
  - detecting the first edge corresponding to an upper boundary in the measurement region and the second edge corresponding to a lower boundary in the measurement region.

14. The method of claim 9, wherein:
the number of the second side image is at least one,
the method further comprising: detecting a first edge and a second edge of the at least one second side image, the at least one second side image being generated from the ROI image, and
the measuring of the thickness of the measurement region comprises:
- obtaining a plurality of measured distances by measuring a distance between the first edge and the second edge in each of a plurality of side images including the first side image and the at least one second image; and
- measuring the thickness of the measurement region based on at least one of the mean, standard deviation, minimum distance, and maximum distance of the plurality of the measured distances.

15. The method of claim 9, wherein the measuring the thickness of the measurement region comprises:
- obtaining the maximum distance between the first edge and the second edge; and
- measuring the thickness of the measurement region based on the maximum distance.

16. The method of claim 14, further comprising:
- controlling to distinctly display the first edge and the second edge of a max side image among the plurality of side images and the first edges and the second edges of the other side images, the measured distance of the maximum side image being the maximum distance.

17. The 3D ultrasound system of claim 6, wherein the controller is configured to display, on a screen, at least one of the mean, standard deviation, minimum distance and maximum distance of the plurality of the measured distances.

18. The method of claim 14, further co sing:
- displaying, on a screen, at least one of the mean, standard deviation, minimum distance and maximum distance of the plurality of the measured distances.

* * * * *